United States Patent [19]
Funderburk et al.

[11] Patent Number: 6,056,718
[45] Date of Patent: May 2, 2000

[54] MEDICATION INFUSION SET

[75] Inventors: Jeffery V. Funderburk, Granada Hills; Leif N. Bowman, Westminster, both of Calif.

[73] Assignee: MiniMed Inc., Sylmar, Calif.

[21] Appl. No.: 09/034,626

[22] Filed: Mar. 4, 1998

[51] Int. Cl.⁷ .................... A61M 11/00; A61M 5/178; A61M 5/00
[52] U.S. Cl. .................. 604/93; 604/161; 604/164; 604/263; 604/264
[58] Field of Search .................. 604/164, 165, 604/167, 169, 174, 175, 244, 245, 256, 263, 264, 272, 161, 162, 93

[56] References Cited

U.S. PATENT DOCUMENTS

| | | | |
|---|---|---|---|
| 4,245,635 | 1/1981 | Kontos | 128/214.4 |
| 4,880,412 | 11/1989 | Weiss | 604/165 |
| 4,950,252 | 8/1990 | Luther et al. | 604/198 |
| 5,201,717 | 4/1993 | Wyatt et al. | 604/192 |
| 5,346,479 | 9/1994 | Schneider | 604/164 |
| 5,356,389 | 10/1994 | Willing | 604/164 |
| 5,423,775 | 6/1995 | Cannon | 604/283 |
| 5,584,813 | 12/1996 | Livingston et al. | 604/177 |
| 5,728,071 | 3/1998 | Watson et al. | 604/180 |
| 5,762,632 | 6/1998 | Whisson | 604/171 |

OTHER PUBLICATIONS

"Tape Tips And Other Infusion Site Information"; Betty Brackenridge, MS,RD,CDE; Janet Brayant, RN, CETN; Ruth Farkas–Hirsch, MS, RN, CDE; Madelein Fernandez, LPN; Paul Schickling, RPH, CDE; Leigh Steed, RN, CDE; & Suzanne Strowig, MSN, RN, CDE; MiniMed Technologies Inc. 1995; pp. 3–11.

*Primary Examiner*—Mark O. Polutta
*Assistant Examiner*—Patricia M. Bianco
*Attorney, Agent, or Firm*—MiniMed Inc.

[57] ABSTRACT

An improved medication infusion set is provided of the type having a soft cannula for subcutaneous delivery of a selected medication to a patient. The infusion set comprises a cannula housing having a soft cannula protruding therefrom and a self-sealing septum mounted at an upstream end of the cannula. The cannula housing is initially assembled with an insertion hub having an elongated insertion needle extending through the septum and cannula for transcutaneously placing the cannula followed by separation of the insertion hub from the cannula housing. An infusion hub is then assembled with the cannula housing and includes a short infusion needle for coupling the cannula with the selected medication supplied from a source via a length of infusion tubing. The infusion hub includes a protective shroud plate protruding beyond a tip end of the infusion needle to minimize risk of patient contact therewith, and adapted for slide-fit reception into a matingly shaped slot formed in the cannula housing to insure a one-way and high strength interconnection between the cannula housing and infusion hub. Releasable latch members interlock the infusion hub with the cannula housing in a manner permitting periodic separation when desired.

35 Claims, 7 Drawing Sheets

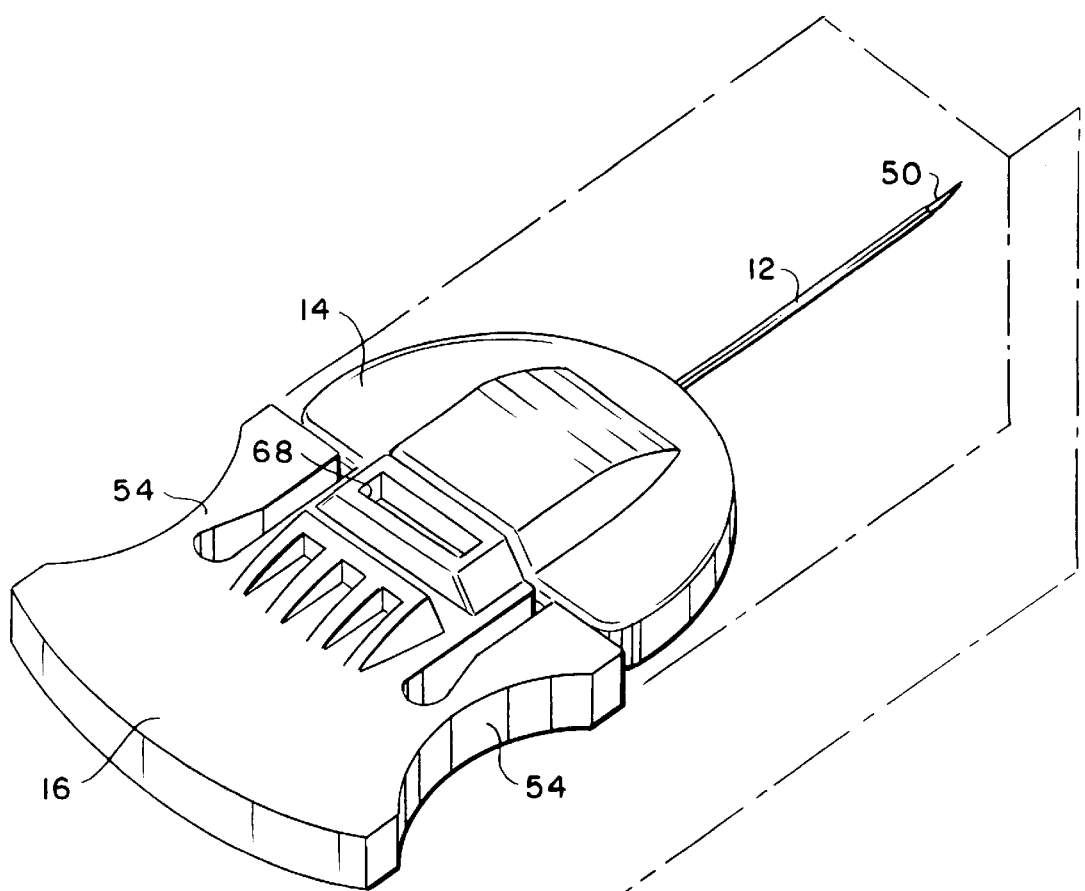
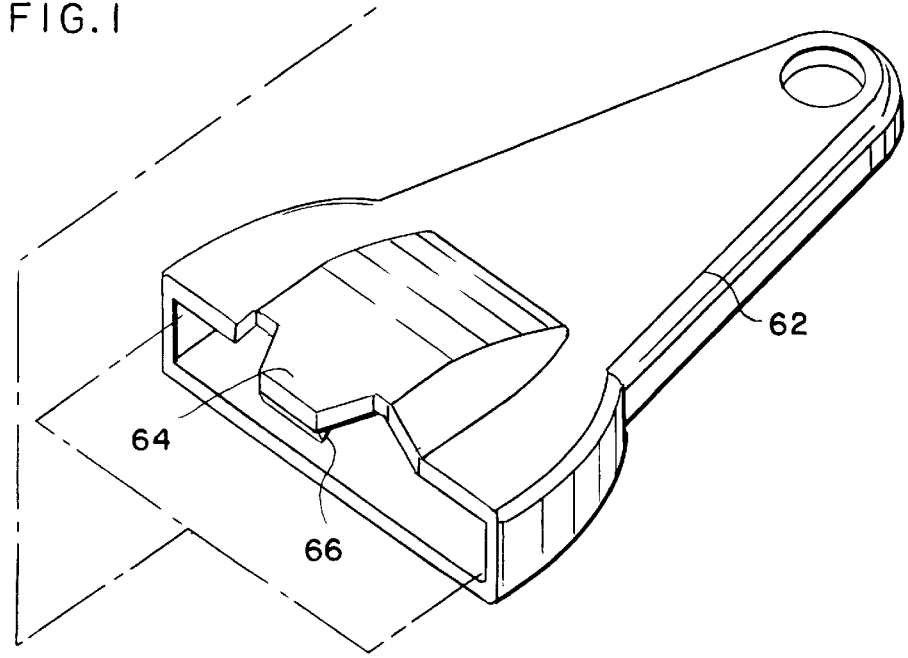
FIG.1

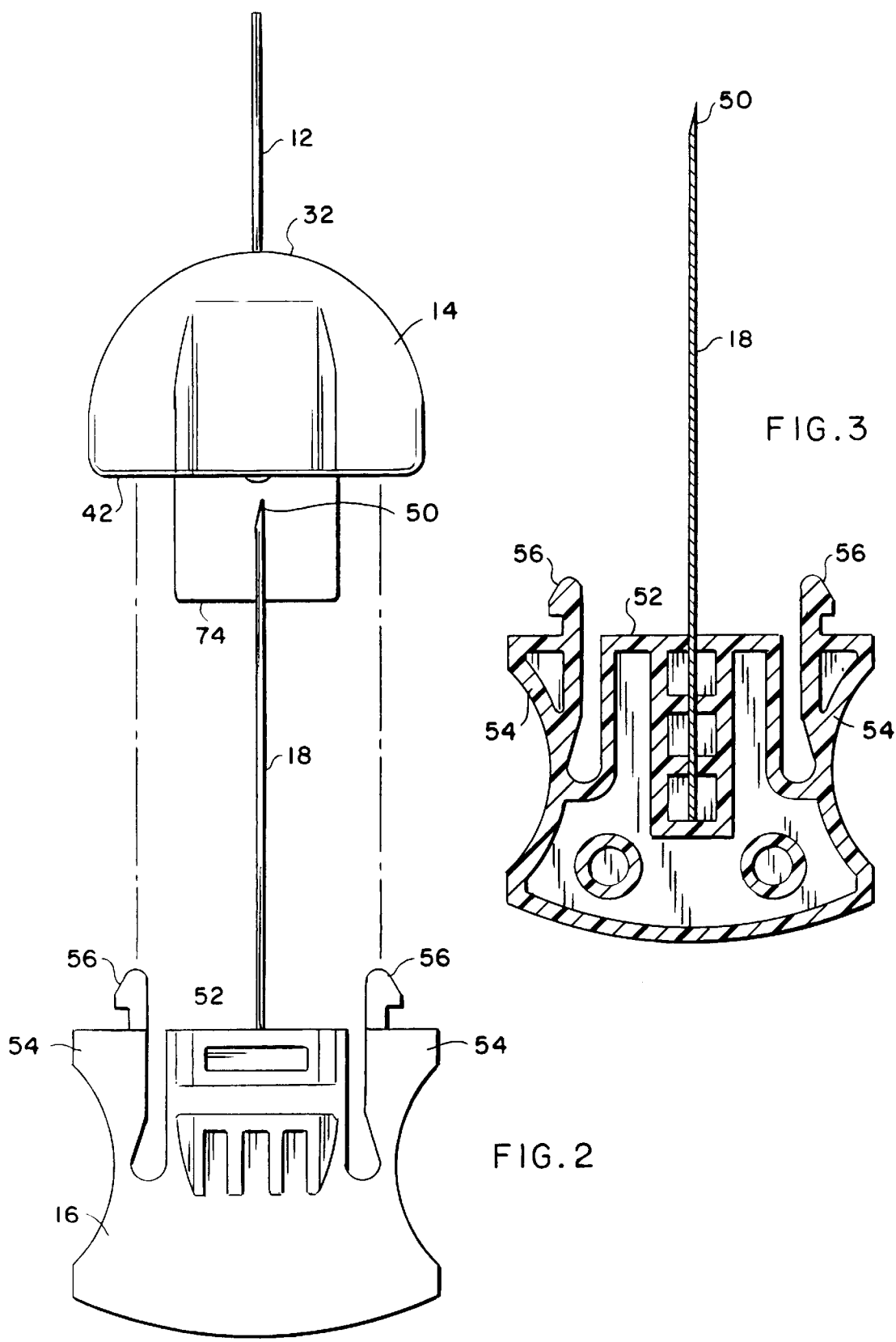

MEDICATION INFUSION SET

BACKGROUND OF THE INVENTION

This invention relates generally to devices and methods for delivering a selected medication or other therapeutic fluid to a patient at a subcutaneous infusion site. More particularly, this invention relates to an improved medication infusion set of the type having a soft or flexible cannula adapted for subcutaneous placement, in combination with an infusion needle associated with a protective shroud plate to minimize risk of patient contact therewith while providing a high strength and unidirectional releasible coupling with the cannula.

Medication injection or infusion sets are generally well known in the art, to include a relatively soft and flexible cannula providing a transcutaneous pathway through which a selected medication or other therapeutic fluid can be administered to a patient at a selected subcutaneous site. In a common form, the soft cannula is carried by a compact housing to include a resilient self-sealing septum mounted at an upstream end of the cannula. This cannula housing is initially assembled with an insertion needle extending through the septum and cannula, wherein the insertion needle is manipulated to pierce the patient's skin to place the cannula transcutaneously, followed by withdrawal of the insertion needle to leave the soft cannula in place on the patient. The selected medication is then coupled to the cannula, typically by means of a length of infusion tubing connected to a medication source, to deliver the medication through the cannula to the patient. In one configuration, the infusion tubing is connected to the cannula housing at a location downstream from the septum as shown, for example, in U.S. Pat. Nos. 4,755,173; 5,176,662; and 5,257,980. In another arrangement, the infusion tubing is coupled to the cannula housing by means of an infusion needle passed through the septum as shown, for example, in U.S. Pat. No. 5,522,803.

Subcutaneous infusion sets of the above-described type are used extensively to administer medication to a patient over an extended period of time. For example, such infusion sets are used with medication infusion pumps of the type described in U.S. Pat. Nos. 4,562,751; 4,685,903; 5,080,653; and 5,097,122 for delivering a long-term medication such as insulin in a continuous or programmable dosage to the patient. With such medication delivery systems, however, it is known that the medication source must be periodically disconnected from the cannula. For example, it has been recognized that the infusion set should be replaced every few days, whereby it is necessary for the patient to uncouple the medication source from an in situ cannula upon removal thereof from the patient, and to recouple the infusion tubing with a second, newly placed cannula. In addition, some patients may briefly disconnect the medication source and related infusion tubing from the cannula to facilitate certain activities, such as swimming or bathing, or participation in certain athletic activities, etc.

In this regard, an optimal medication infusion set is adapted for low profile and inobtrusive placement on the patient, while permitting quick and safe periodic disconnection from and reconnection to the medication source. To this end, use of an infusion needle adapted for coupling through the self-sealing septum provides a quick and easy structure for connecting and disconnecting the medication source from the cannula, but also subjects the patient to undesirable needle sticks from exposure to the infusion needle. Moreover, this arrangement requires a strong and reliable mechanical interlock between the cannula housing and the infusion needle to insure consistent and proper interengagement without inadvertent component separation, while permitting quick and easy and repeated disconnection when desired. All of these features are desirably provided in an infusion set constructed from relatively simple and preferably disposable components which can be manufactured in a cost-efficient manner from medical grade plastic or the like.

The present invention provides an improved medication infusion set designed to meet these features and advantages, by including an infusion needle associated with a protective shroud plate. The shroud plate closely overlies and substantially encases the infusion needle in a manner minimizing risk of patient contact therewith, while additionally providing a strong guide structure for keyed or one-way interconnection with a cannula housing.

SUMMARY OF THE INVENTION

In accordance with the invention, an improved medication infusion set is provided for use in delivering medication through a soft cannula to a selected subcutaneous infusion site on a patient. The soft cannula is supported by a compact and low profile cannula housing which includes a self-sealing septum disposed at a proximal or upstream end of the cannula. An infusion hub is provided with latch means for releasible assembly with the cannula housing, and includes a short infusion needle coupled via infusion tubing or the like to a source of the selected medication. The infusion hub includes a protective shroud plate which closely overlies and substantially encases the infusion needle to reduce risk of inadvertent patient contact therewith. The protective shroud plate is configured for unidirectional or one-way reception into a matingly shaped slot formed in the cannula housing upon assembly of the components to provide a high strength connection.

In the preferred form on the invention, the cannula housing comprises a compact plastic molding defining an internal bore for seated reception of a proximal end of the soft cannula. A generally cylindrical needle guide is also seated within the cannula housing and has a downstream end press-fitted into the cannula proximal end. The needle guide defines a flared upstream end, and a ball-shaped resilient and self-sealing septum is retained therein by a retainer clip adapted for snap-fit mounting onto the cannula housing.

The cannula housing is initially assembled with an insertion hub which may also be formed from a molded plastic and includes at least one and preferably a pair of resilient latch arms for snap-fit reception into aligned latch ports formed in a proximal face of the cannula housing. The insertion hub carries an elongated insertion needle passed through the septum and needle guide, and further through the soft cannula terminating in a pointed tip end disposed a short distance beyond the distal or downstream end of the cannula. The insertion needle is utilized to pierce the patient's skin at a selected medication infusion site, to transcutaneously place the soft cannula, after which the insertion hub is separated from the cannula housing to withdraw the insertion needle from the cannula.

The infusion hub also comprises a low profile component of molded plastic or the like and carries the infusion needle in flow communication with the source of the selected medication, typically via a length of infusion tubing. The infusion needle protrudes from a distal face of the infusion hub in close association with the protective shroud plate which protrudes at least slightly beyond the tip end of the infusion needle. In a preferred form, the shroud plate comprises a multifaceted and preferably three-sided structure enclosing the infusion needle on three sides to substantially prevent patient contact and accidental needle sticks. The shroud plate is configured for slide-fit reception into a matingly shaped slot formed in the proximal face of the cannula housing, with a one-way fit, for accurate guided reception of the infusion needle through the septum to extend partially into the needle guide. At least one and preferably a pair of resilient latch arms on the infusion hub are provided for snap-fit reception into the latch ports on the cannula housing to releasibly interlock the components.

In use, the infusion hub is securely coupled with the cannula housing with a high strength interconnection resistant to bending or twisting forces that could otherwise contribute to inadvertent component separation. However, the infusion hub can be quickly and easily disconnected from the cannula housing when desired, for example, when the cannula is replaced or during patient activities requiring temporary disconnection of the medication source. The infusion hub is adapted for quick and easy reconnection to the existing or to a replacement cannula housing, with a simple one-way snap-fit connection, and with the infusion needle substantially concealed from patient contact at all times.

Other features and advantages of the present invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 1 is an exploded perspective view illustrating a medication infusion set formed in accordance with the novel features of the invention, to include a cannula housing assembled with an insertion hub, shown in exploded relation with a needle guard;

FIG. 2 is a top plan view showing the cannula housing and insertion hub in exploded relation;

FIG. 3 is a horizontal sectional view of the insertion hub;

DETAILED DESCRIPTION OF THE PREFERRED EMBODIMENT

Figure 4:
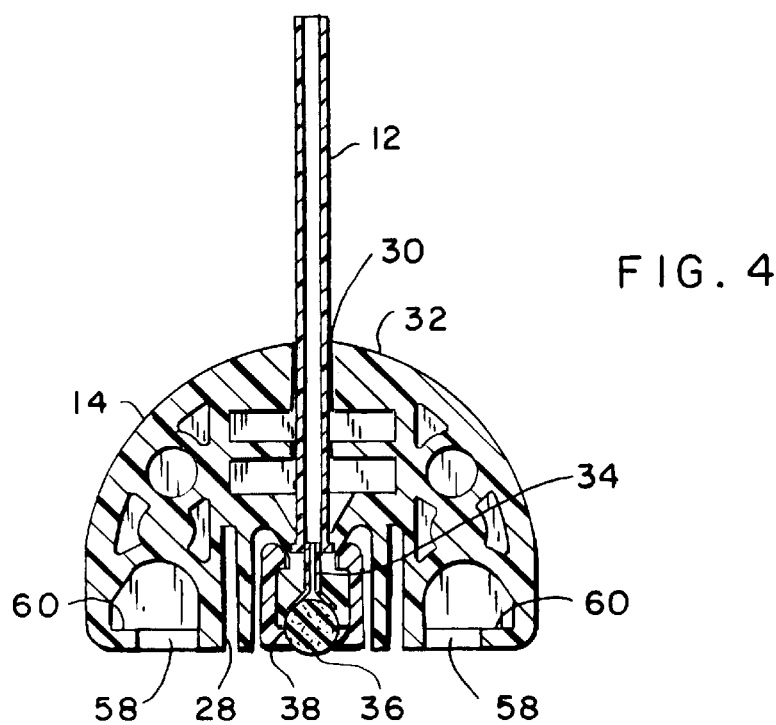
FIG. 4 is a horizontal sectional view of the cannula housing.

As shown in the exemplary drawings, an improved infusion set is provided for use in administering a selected medication to a patient at a selected subcutaneous infusion site. The infusion set comprises a soft and flexible cannula 12 carried by a compact and low profile cannula housing 14. An inserter hub 16 including an insertion needle 18 is initially assembled with the cannula housing 14 for transcutaneously placing the cannula, as viewed in FIGS. 1–6 and 11. Thereafter, an infusion hub 20 including an infusion needle 22 coupled to a source of a selected medication via a length of infusion tubing 24 is assembled with the cannula housing 14 for delivering the medication to the patient, as viewed in FIGS. 7–10. The infusion hub 20 includes a protective shroud plate 26 closely overlying the infusion needle 22 to prevent undesirable needle sticks, wherein the shroud plate 26 slide-fits into a mating slot 28 formed in the cannula housing 14 to provide a one-way and high strength interconnection of the components.

The medication infusion set of the present invention is particularly suited for delivering medication to a patient on a continuous or programmable basis over an extended period of time, such as, for example, the administration of insulin to a diabetic patient by means of a programmable infusion pump of the type described in U.S. Pat. Nos. 4,562,751; 4,685,903; 5,080,653; and 5,097,122. The infusion set comprises a compact, low profile and economical assembly of components adapted for quick and easy transcutaneous placement of the soft cannula 12 at the selected infusion site, followed by quick and easy coupling of the cannula with the selected medication source. The infusion hub 20 and the cannula housing 14 are constructed for facilitated and repeated interconnection with a unidirectional or one-way fit while minimizing risk of patient contact with the infusion needle 18, and further to provide a high strength attachment which is resistant to inadvertent separation in response to bending, twisting, and tension forces. In addition, the infusion hub 20 and associated infusion needle 18 can be disconnected quickly and easily from the cannula housing 14 by the patient as may be required or desired, for example, when replacing the cannula typically at intervals of several days, or when the patient participates in athletic or other activities such as swimming or bathing wherein temporary disconnection of the infusion pump is warranted. Importantly, the infusion hub 20 can be reconnected rapidly and safely by the patient to the existing or to a replacement cannula housing to provide a strong and reliable component interface.

Figure 5:
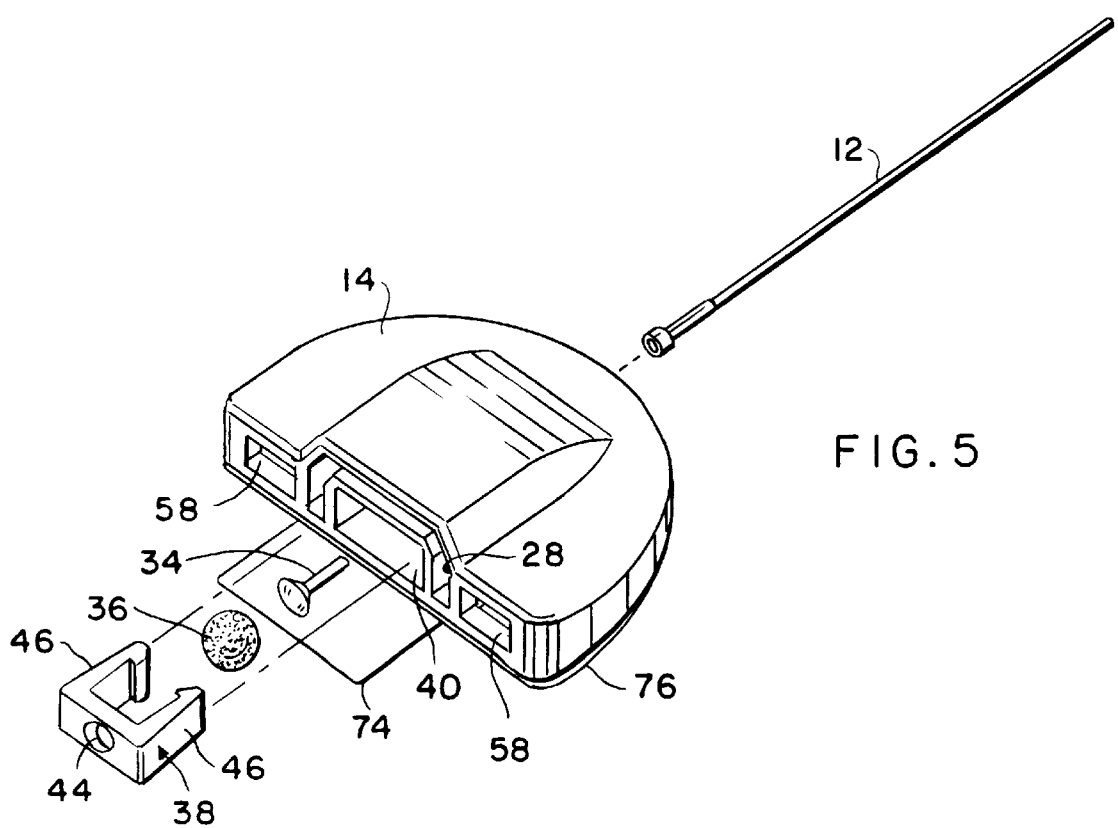
FIG. 5 is an exploded perspective view illustrating assembly of the cannula housing.
Figure 6:
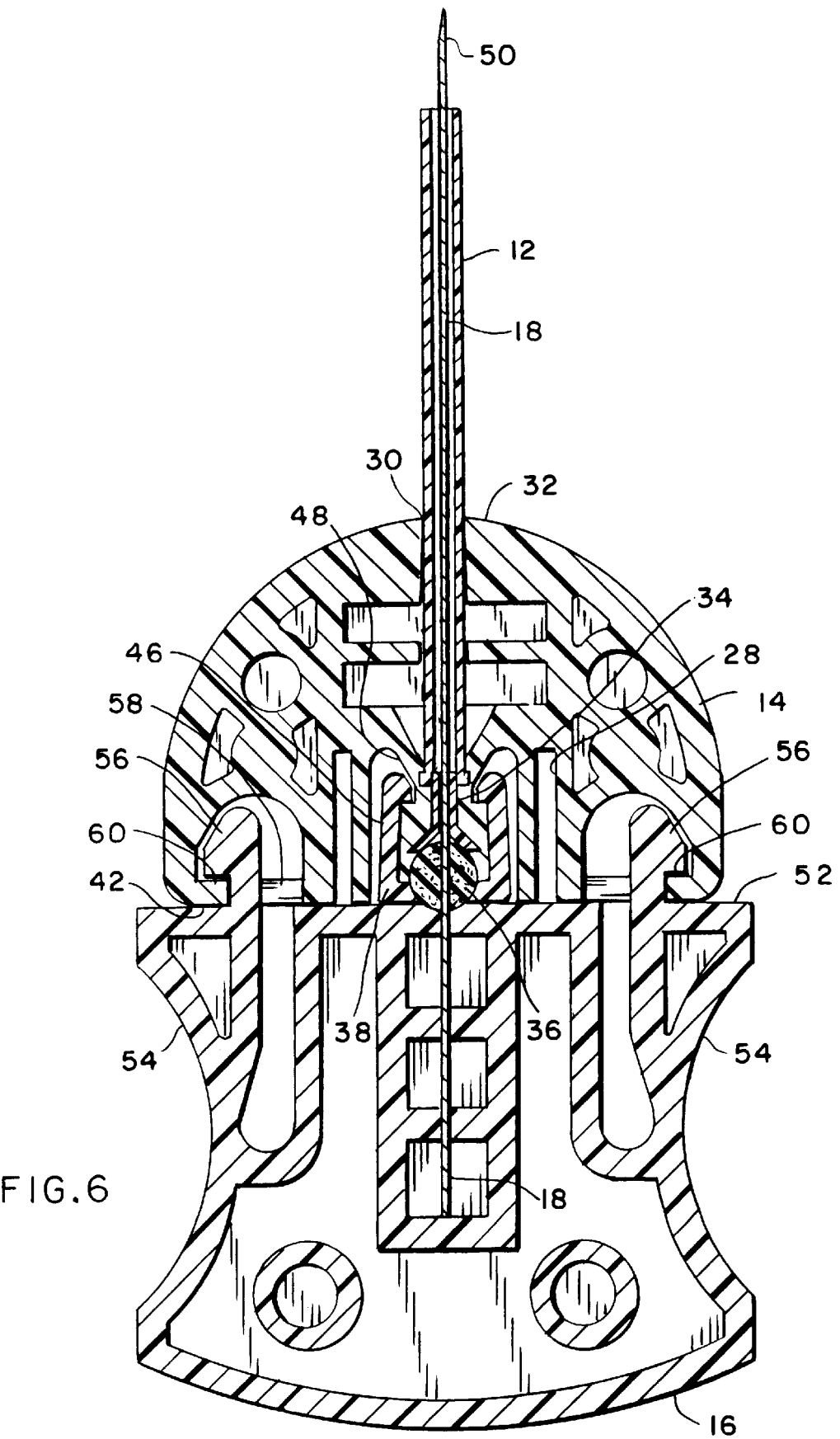
FIG. 6 is a horizontal sectional view showing the cannula housing and insertion hub in assembled relation.
Figure 7:
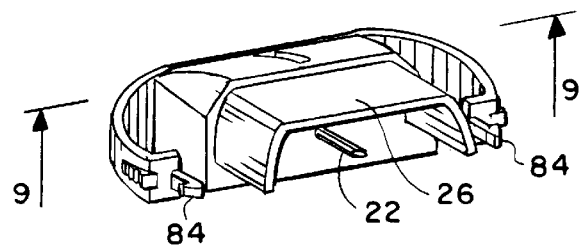
FIG. 7 is a top plan view showing the cannula housing and an infusion hub in exploded relation.
Figure 8:
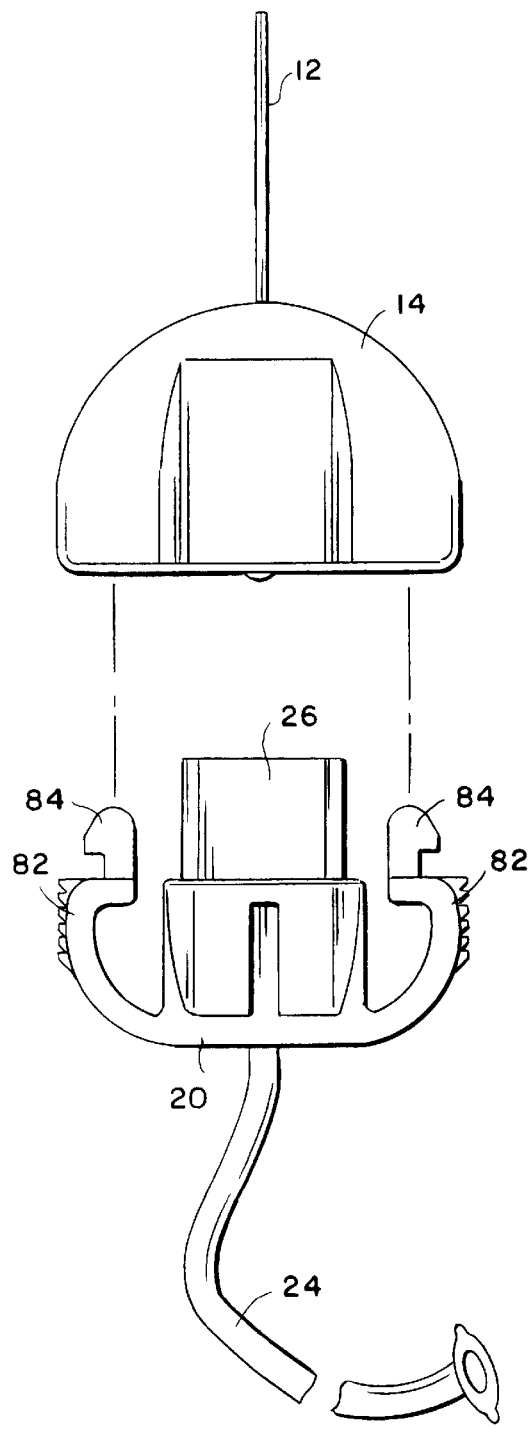
FIG. 8 is a perspective view of the infusion hub shown in FIG. 7, depicting the distal or downstream face thereof.
Figure 9:
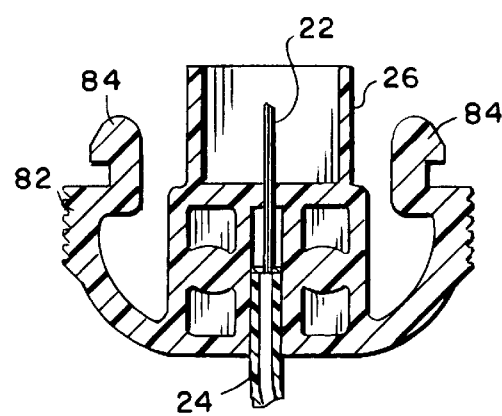
FIG. 9 is a horizontal sectional view of the infusion hub.
Figure 10:
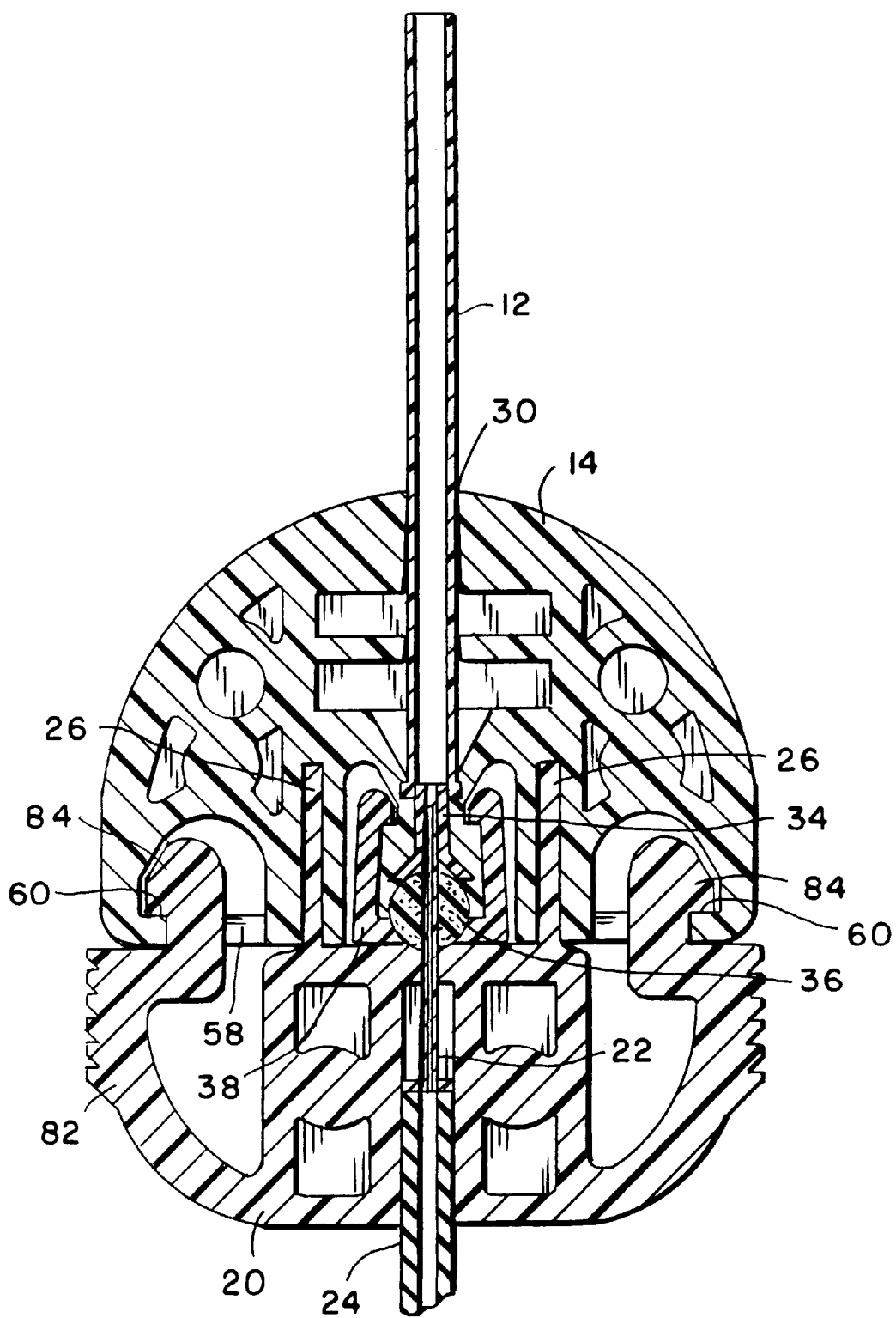
FIG. 10 is a horizontal sectional view showing the cannula housing and infusion hub in assembled relation.

The cannula housing 14 is shown in detail in FIGS. 4–6, to comprise a compact and low profile component constructed from a medical grade molded plastic which is clear or transparent to facilitate viewing of the infusion site. The cannula housing defines a bore 30 extending therethrough and adapted to receive and support an upstream or proximal end of the soft cannula 12, with a distal end of the cannula protruding outwardly from a smoothly rounded distal face 32 of the cannula housing. In the preferred form, the proximal end of the cannula 12 is press-fit mounted onto a downstream end of a needle guide 34 formed from stainless steel or the like, and these assembled components are compression fitted into the bore 30. In this regard, for facilitated assembly, the bore 30 may be formed in the plastic molded cannula housing 14 in the form of a downwardly open channel.

The upstream end of the needle guide 34 is flared outwardly to form a radially enlarged and generally conical seat for receiving and supporting a resilient self-sealing septum 36 in the form of a ball. The septum 36 is securely retained within the flared end of the needle guide 34 by a small generally U-shaped retainer clip 38. This retainer clip 38 is sized and shaped to fit into an open cavity 40 formed in a proximal face 42 of the cannula housing 14, with a centrally located needle port 44 formed in the clip 38 to permit needle access via the septum 36 and needle guide 34 with the cannula 12, as will be described in more detail. The opposing legs of the U-shaped retainer clip 38 include in-turned latch feet 46 for snap-fit engagement into latch detents 48 formed by the cannula housing 14 on opposite sides of the bore 30, to lock the retainer clip 38 onto the cannula housing. The ball-shaped septum conveniently mounts within the flared end of the needle guide in a self-centered manner, and without reference to orientation, to provide a maximized septum surface area and internal volume within a minimum space.

The cannula housing 14 and related cannula 12, as described above, are shown in FIGS. 1 and 6 in preassembled relation with the insertion hub 16 for use in transcutaneously placing the cannula 12 on the patient at the selected subcutaneous infusion site. To this end, the insertion hub 16 also comprises a compact and low profile component which is preferably formed from molded plastic with an overall size and shape generally conforming with the cannula housing 14. As shown best in FIGS. 2 and 3, the insertion hub 16 rigidly supports a rear or proximal end of the insertion needle 18 which protrudes from the hub 16 and terminates in a pointed distal end tip 50. The insertion needle 18 is adapted to pierce the ball-shaped septum 36 and to extend through the needle guide 34 and further through the soft cannula 12, to position the sharp tip 50 at least slightly beyond the distal end tip of the cannula. In this orientation, a distal face 52 of the insertion hub 16 is substantially butted against the proximal face 42 of the cannula housing 14 (FIGS. 1 and 6). A pair of resilient latch arms 54 on the insertion hub 16 having out-turned latch fingers 56 thereon are received into a corresponding pair of open latch ports 58 formed in the proximal face 42 of the cannula housing, and these latch fingers 56 snap-fit engage with undercut recesses 60 on the cannula housing to retain the insertion hub 16 and the cannula housing 14 in assembled relation.

A shell-shaped needle guard 62 as shown in FIG. 1 is normally provided for mounting onto the preassembled insertion hub 16 and cannula housing 14, to protect against undesired contact with the insertion needle 18. The needle guard 62 may also comprise a simple plastic molding having a size and shape to fit over the protruding insertion needle 16 and the soft cannula 12 thereon, and to include a rearwardly extending clip segment 64 having a latch tooth 66 for releasible reception into an upwardly open notch 68 formed in an upper surface of the insertion hub 16.

Figure 11:
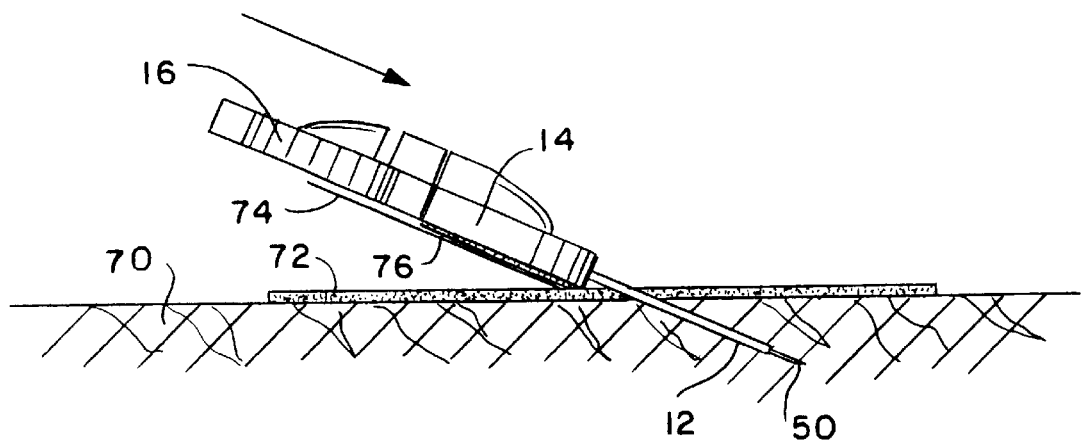
FIG. 11 is a fragmented sectional view illustrating use of the insertion hub for placing the cannula housing on a patient.
Figure 12:
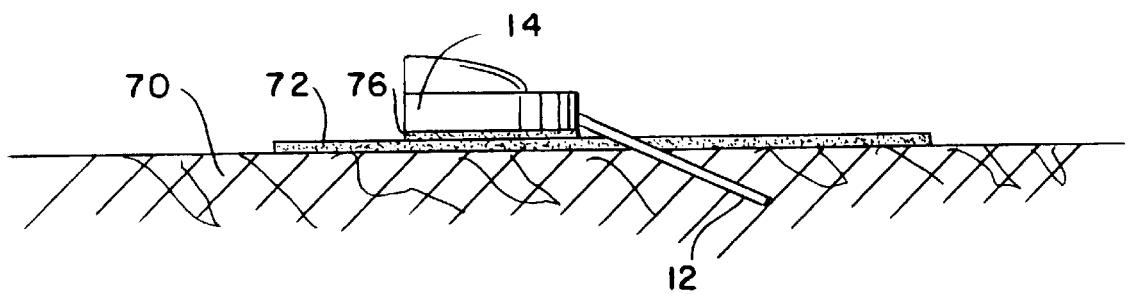
FIG. 12 is a fragmented sectional view similar to FIG. 11, and depicting the cannula housing seated on the patient.

When placement of the cannula 12 on the patient is desired, the needle guard 62 is removed from the preassembled insertion hub and cannula housing to expose the insertion needle 18, as viewed in FIG. 1. The preassembled components are then manipulated as a unit, primarily by grasping the insertion hub 16, to pierce the patient's skin 70 at a selected infusion site as shown in FIG. 11. In this regard, in a preferred placement procedure, the infusion site is prepared by initial cleansing followed by placement of a mounting substrate in the form of a patch 72 mounted onto the skin 70 by means of a suitable hypoallergenic or non-irritating adhesive, such as a patch marketed by Wound Management Division of Smith+Nephew of Largo, Fla. under the product designation OpSite IV 3000. The patch 72 provides a smoother and flatter mounting base of improved lateral stability for more secure mounting of the cannula housing 14, as compared to direct placement onto the patient's skin 70, and has an attachment surface area significantly greater than the underside surface area of the cannula housing. The insertion needle 18 can be inserted transcutaneously by placement directly through the patch 72, typically at an angle to the skin 70 of about 30–45 degrees, to transcutaneously place the cannula 12, with the patch 72 supporting the skin in the region of the needle pierce point. When the cannula is properly placed, the insertion hub 16 can be separated from the cannula housing 14 by squeezing inwardly on the latch arms 54 to permit withdrawal of the insertion needle thereby leaving the cannula 12 in position on the patient. The cannula housing 14 is then secured to the patient by removing a peel-off paper strip 74 from the underside thereof to expose an adhesive layer 76 suited for secure attachment to the patch 72, as viewed in FIG. 12.

In the preferred form, the adhesive layer 76 securing the cannula housing 14 to the patch 72 is chosen for a strong and stable attachment, with the broader and larger surface area of the patch in turn providing a secure and stable mounting relative to the patient's skin 70. As a result, the attachment force retaining the cannula housing 14 to the patch 72, as well as the attachment force retaining the patch 72 to the patient's skin, can significantly exceed the attachment force otherwise achievable by adhering the cannula housing 14 directly to the patient's skin. Accordingly, the cannula housing and the associated cannula 12 are anchored in a manner such that partial pull-out of the cannula is unlikely to occur during normal patient movement and/or inadvertent tugging or pulling of the infusion set. When removal of the cannula is desired, the patch 72 and cannula housing 14 are removed as a unit for disposal. Alternately, it will be understood that the cannula housing 14 may be adhered directly to the patient's skin 70, in the event that the patch 72 is not used.

Following placement of the cannula 12 on the patient, the infusion hub 20 is coupled quickly and easily with the cannula housing 14 for supplying the selected medication to the patient. More particularly, as shown in FIGS. 7–10, the infusion hub 20 also comprises a compact and low profile component of medical grade molded plastic with an overall size and shape for connection to the cannula housing. The infusion hub 20 defines an internal bore 78 for seated reception of the infusion needle 22. A rear end of the infusion needle is positioned for press-fit connection to the length of infusion tubing 24 which, as previously described, is coupled in turn to the appropriate medication source such as a medication infusion pump (not shown). A forward or tip end of the infusion needle 22 protrudes outwardly from a distal face 80 of the infusion hub 20, with a length sufficient to extend through the resilient septum 36 and partially into the metal needle guide 34 within the cannula housing 14, when the infusion hub is connected to the cannula housing. Accordingly, with this geometry, the infusion needle 22 does not protrude beyond the needle guide 34 into the soft cannula 12, thereby minimizing or eliminating risk of needle-caused damage to the soft cannula. A pair of resilient latch arms 82 also project from the distal face 80 of the infusion hub 20 and include out-turned latch fingers 84 for snap-fit engagement into the latch recesses 60 formed in the cannula housing 14 to releasibly lock the components together, with the infusion needle 22 coupling the infusion tubing 24 with the cannula 12.

In accordance with one primary aspect of the invention, the shroud plate 26 extends from the distal face of the infusion hub 20 to closely overlie and protect the infusion needle. As shown, the shroud plate 26 comprises a multi-faceted and preferably three-sided structure extending over the top and both sides of the infusion needle 22, and projecting from the infusion hub at least slightly beyond the distal end tip of the infusion needle. With this construction, the shroud plate substantially and effectively shields the infusion needle 22 against significant risk of patient contact therewith during manipulation of the infusion hub to connect or disconnect the infusion tubing from the cannula, thereby substantially preventing undesirable needle sticks.

Moreover, the protective shroud plate 26 presents a keyed structure for unidirectional or one-way connection of the infusion hub 20 with the cannula housing 14, in a manner providing a strong interconnection with accurate guided coupling of the infusion needle 22 through the septum 36 and into the needle guide 34, yet additionally permitting quick and easy disconnection when desired. Specifically, the shroud plate 26 is sized and shaped for slide-fit reception into the matingly shaped and thus preferably three-sided slot 28 formed in the proximal face 42 of the cannula housing 14, to extend over the top and at both sides of the retainer clip 38. The shroud plate 26 slidably fits into the slot 28 in one orientation only, thereby properly positioning and aligning the infusion needle 22 with the retainer clip port 44. As the shroud plate 26 is advanced into the mating slot 28, the needle 22 correspondingly advances through the septum and partially into the needle guide 34, while the latch arms 82 advance into the latch ports 58 for snap-fit connection of the infusion hub 20 to the cannula housing 14. When fully connected, the shroud plate 26 presents a broad and multi-faceted surface area engaging the cannula housing within the slot 28 to provide a strong interconnection which is highly resistant to bending, twisting and other forces otherwise contributing to potential inadvertent separation of the components.

However, when disconnection of the components is desired, the latch arms 82 are quickly and easily pressed inwardly to release from the associated latch recesses 60, to permit simple slide-apart separation of the infusion hub 20 from the cannula housing 14. The shroud plate 26 presents a central housing structure between the latch arms 82 to block excess displacement when the latch arms are pressed inwardly, thereby protecting the latch arms against permanent deformation and/or breakage, and correspondingly permitting repeated connection and disconnection of the infusion hub. Importantly, upon such separation, the septum 36 seals the upstream end of the cannula to maintain sterility. During this separated condition, the patient may participate in a variety of activities such as athletic events, swimming or bathing, wherein it may be desirable to avoid exposure of the medication source such as an infusion pump to physical jarring or to water, etc. Alternately, with the infusion hub 20 separated from the cannula housing 14, other medications can be administered to the patient by means of a syringe or the like piercing the septum 36. Still further, separation of the infusion hub 20 from the cannula housing 14 is typically desired at intervals of a few days to permit removal of an in situ cannula and replacement with a new one. In all cases, the infusion hub 20 is quickly and easily reconnected to the associated cannula housing 14 with a simple sliding and snap-fit one-way attachment.

A variety of further modifications and improvements in and to the improved medication infusion set of the present invention will be apparent to persons skilled in the art. Accordingly, no limitation on the invention is intended by way of the foregoing description and accompanying drawings, except at set forth in the appended claims.

What is claimed is:

1. A medication infusion set for transcutaneous delivery of a selected medication to a patient, said infusion set comprising:

a cannula housing having a soft cannula mounted thereon with a distal end of said cannula protruding from said cannula housing, a resilient self-sealing septum mounted on said cannula housing generally at a proximal end of said cannula for normally closing said cannula proximal end, and a retainer mounted within said cannula housing for retaining said septum within said cannula housing, wherein said retainer comprises a retainer clip for snap-fit mounting within said cannula housing, said retainer clip having a needle port formed therein; and an infusion hub having an infusion needle mounted thereon with a distal end of said infusion needle protruding from said infusion hub and being adapted for connection to a source of the selected medication, said infusion needle being adapted for insertion through said septum for coupling with said cannula, wherein said infusion hub further includes a protective shroud protruding therefrom in overlying relation with said infusion needle, said shroud being a guide slidably insertable into a generally matingly shaped slot formed in said cannula housing for one-way guided reception of said infusion needle through said septum and wherein said cannula housing and said infusion hub further includes releasibly interengageable latch members for releasibly connecting said infusion hub to said cannula housing with said infusion needle inserted through said septum.

2. The medication infusion set of claim 1, further including a rigid tubular needle guide interposed between said septum and said cannula proximal end.

3. The medication infusion set of claim 2, wherein said needle guide has a downstream end press-fit into said cannula proximal end.

4. The medication infusion set of claim 3, wherein said needle guide and said cannula proximal end are press-fit mounted into an open-sided channel formed in said cannula housing.

5. The medication infusion set of claim 2, wherein said infusion needle has a length to extend through said septum and partially into said needle guide when said cannula housing and infusion hub are connected together.

6. The medication infusion set of claim 2, wherein said needle guide comprises a metal needle guide.

7. The medication infusion set of claim 1, further including an insertion hub having an insertion needle mounted thereon with a distal end protruding therefrom, said insertion needle being insertable through said septum to extend through said cannula and terminating with a sharp distal end tip disposed at least slightly beyond a distal end of said cannula, said insertion hub being adapted for transcutaneously placing said cannula on a patient and thereafter being withdrawable from said cannula and cannula housing.

8. The medication infusion set of claim 7, wherein said cannula housing has an underside surface with an adhesive layer thereon, and further including an adhesive patch for placement onto a patient, said insertion needle being adapted for transcutaneously placing said cannula by piercing said patch, said adhesive layer on said cannula housing securing said cannula housing to said patch.

9. The medication infusion set of claim 8, wherein said adhesive patch has an area of attachment to the patient's skin substantially greater than the area of said underside surface on said cannula housing.

10. The medication infusion set of claim 7, wherein said latch members comprise at least one resilient latch arm protruding from said insertion hub and at least one latch port having a latch detent therein formed on said cannula housing for snap-fit and releasable engagement with said latch arm.

11. The medication infusion set of claim 7, wherein said latch members comprise a pair of resilient latch arms protruding from said insertion hub at opposite sides of said insertion needle, and a corresponding pair of latch ports each having a latch detent therein formed on said cannula housing for snap-fit and releasable engagement with said latch arms.

12. The medication infusion set of claim 7, further including a needle guard for removable mounting onto said insertion hub when said insertion hub is assembled with said cannula housing to encase said insertion needle and said cannula protruding from said cannula housing.

13. The medication infusion set of claim 1, wherein said cannula proximal end is press-fit mounted into an open-sided channel formed in said cannula housing.

14. The medication infusion set of claim 1, further including a rigid tubular needle guide interposed between said septum and said cannula proximal end, said needle guide having a downstream end press-fit connected to said cannula proximal end, and an upstream end flared outwardly to form a generally conical seat for receiving and supporting said septum, and further including a retainer mounted within said cannula housing for retaining said septum within said conical seat.

15. The medication infusion set of claim 1, further including infusion tubing coupled to said infusion hub for coupling said infusion needle to the medication source.

16. The medication infusion set of claim 1, wherein said latch members comprise at least one resilient latch arm protruding from said infusion hub and at least one latch port having a latch detent therein formed on said cannula housing for snap-fit and releasable engagement with said latch arm.

17. The medication infusion set of claim 1, wherein said latch members comprises a pair of resilient latch arms protruding from said infusion hub at opposite sides of said shroud, and a corresponding pair of latch ports each having a latch detent therein formed on said cannula housing for snap-fit and releasable engagement with said latch arms.

18. The medication infusion set of claim 1, further including an adhesive layer on an underside surface of said cannula housing.

19. The medication infusion set of claim 1, further including an adhesive patch for removable mounting onto the skin of a patient at a selected infusion site, said insertion needle being adapted to pierce said patch and the patient's skin to transcutaneously place said cannula, said adhesive patch being adapted to attach said cannula housing to said patch on the patient's skin.

20. A medication infusion set for transcutaneous delivery of a selected medication to a patient, said infusion set comprising:

a cannula housing having a soft cannula mounted thereon with a distal end of said cannula protruding from said cannula housing, and a resilient self-sealing septum mounted on said cannula housing generally at a proximal end of said cannula for normally closing said cannula proximal end; and an infusion hub having an infusion needle mounted thereon with a distal end of said infusion needle protruding from said infusion hub and being adapted for connection to a source of the selected medication said infusion needle being adapted for insertion through said septum for coupling with said cannula, wherein said infusion hub further includes a protective shroud plate protruding therefrom in overlying relation with said infusion needle said shroud plate being slidably insertable into a generally matingly shaped slot formed in said cannula housing for guided reception of said infusion needle through said septum, wherein said cannula housing and said infusion hub further includes releasibly interengageable latch members for releasibly connecting said infusion hub to said cannula housing with said infusion needle inserted through said septum, and wherein said shroud plate comprises a plurality of generally planar facets, said slot formed in said cannula housing being generally matingly shaped for one-way reception of said shroud plate.

21. The medication infusion set of claim 20, wherein said shroud plate extends over the top and at opposite sides of said infusion needle.

22. The medication infusion set of claim 20, wherein said shroud plate extends from said infusion hub at least slightly beyond a distal end of said infusion needle.

23. A medication infusion set for transcutaneous delivery of a selected medication to a patient, said infusion set comprising:

a cannula housing having a soft cannula mounted thereon with a distal end of said cannula protruding from said cannula housing, and a resilient self-sealing septum mounted on said cannula housing generally at a proximal end of said cannula for normally closing said cannula proximal end; and an infusion hub having an infusion needle mounted thereon with a distal end of said infusion needle protruding from said infusion hub and being adapted for connection to a source of the selected medication, said infusion needle being adapted for insertion through said septum for coupling with said cannula, wherein said infusion hub further including a protective shroud plate of multifaceted configuration protruding therefrom in overlying relation with said infusion needle and projecting from said infusion hub at least slightly beyond a distal tip end of said infusion needle, said shroud plate being slidably insertable into a generally matingly shaped slot formed in said cannula housing for one-way guided reception of said infusion needle through said septum, and wherein said cannula housing and said infusion hub further including releasibly interengageable latch members for releasibly connecting said infusion hub to said cannula housing with said infusion needle inserted through said septum.

24. The medication infusion set of claim 23, wherein said latch members comprise a pair of resilient latch arms protruding from said infusion hub at opposite sides of said shroud plate, and a corresponding pair of latch ports each having a latch detent therein formed on said cannula housing for snap-fit and releasable engagement with said latch arms.

25. The medication infusion set of claim 23, further including an insertion hub having an insertion needle mounted thereon with a distal end protruding therefrom, said insertion needle being insertable through said septum to extend through said cannula and terminating with a sharp distal end tip disposed at least slightly beyond a distal end of said cannula, said insertion hub being adapted for transcutaneously placing said cannula on a patient and thereafter being withdrawable from said cannula and cannula housing.

26. A medication infusion set for transcutaneous delivery of a selected medication to a patient, said infusion set comprising:

a cannula housing;

a soft cannula;

a rigid tubular needle guide having a downstream end press-fit mounted with a proximal end of said soft cannula, said needle guide and said cannula proximal end being carried within a bore formed in said cannula housing with a distal end of said cannula protruding from said cannula housing, said needle guide having an upstream end flared outwardly in a generally conical configuration;

a resilient self-sealing septum; and a retainer for retaining said septum seated within said flared upstream of said needle guide, wherein said retainer fits within the cannula housing.

27. The medication infusion set of claim 26, wherein said needle guide downstream end is press-fitted into said cannula proximal end.

28. The medication infusion set of claim 26, wherein said needle guide and said cannula proximal end are press-fit mounted within an open-sided channel formed in said cannula housing.

29. The medication infusion set of claim 26, wherein said needle guide comprises a metal needle guide.

30. The medication infusion set of claim 26, wherein said septum comprises a self-sealing ball.

31. The medication infusion set of claim 26, wherein said retainer comprises a retainer clip for snap-fit mounting onto said cannula, said retainer clip having a needle port formed therein.

32. The medication infusion set of claim 26, wherein said infusion needle has a length to extend through said septum and partially into said needle guide and defining a distal end tip terminating short of said cannula.

33. A medication infusion set for transcutaneous delivery of a selected medication to a patient, said infusion set comprising:

a cannula housing having a soft cannula mounted thereon with a distal end of said cannula protruding from said cannula housing, and a resilient self-sealing septum mounted on said cannula housing generally at a proximal end of said cannula for normally closing said cannula proximal end; and an infusion hub having an infusion needle mounted thereon with a distal end of said infusion needle protruding from said infusion hub and being adapted for connection to a source of the selected medication, said infusion needle being adapted for insertion through said septum for coupling with said cannula, wherein said infusion hub further includes a protective shroud protruding therefrom in overlying relation with said infusion needle, said shroud being a guide slidably insertable into a generally matingly shaped slot formed in said cannula housing for one-way guided reception of said infusion needle through said septum, wherein said cannula housing and said infusion hub further includes releasibly interengageable latch members for releasibly connecting said infusion hub to said cannula housing with said infusion needle inserted through said septum, and wherein said septum comprises a resilient self-sealing ball.

34. A medication infusion set for transcutaneous delivery of a selected medication to a patient, said infusion set comprising:

a cannula housing having a soft cannula mounted thereon with a distal end of said cannula protruding from said cannula housing, and a resilient self-sealing septum mounted on said cannula housing generally at a proximal end of said cannula for normally closing said cannula proximal end; and an infusion hub having an infusion needle mounted thereon with a distal end of said infusion needle protruding from said infusion hub and being adapted for connection to a source of the selected medication, said infusion needle being adapted for insertion through said septum for coupling with said cannula, wherein said infusion hub further including a protective shroud plate of multifaceted configuration protruding therefrom in overlying relation with said infusion needle and projecting from said infusion hub at least slightly beyond a distal tip end of said infusion needle, said shroud plate being slidably insertable into a generally matingly shaped slot formed in said cannula housing for one-way guided reception of said infusion needle through said septum, wherein said cannula housing and said infusion hub further including releasibly interengageable latch members for releasibly connecting said infusion hub to said cannula housing with said infusion needle inserted through said septum, and wherein said shroud plate has a three-sided construction.

35. A medication infusion set for transcutaneous delivery of a selected medication to a patient, said infusion set comprising:

a cannula housing;

a soft cannula;

a rigid tubular needle guide having a downstream end press-fit mounted with a proximal end of said soft cannula, said needle guide and said cannula proximal end being carried within a bore formed in said cannula housing with a distal end of said cannula protruding from said cannula housing, said needle guide having an upstream end flared outwardly in a generally conical configuration;

a resilient self-sealing septum; and a retainer for retaining said septum seated within said flared upstream of said needle guide, wherein said needle guide downstream end is press-fitted into said cannula proximal end, and wherein a channel is formed in an underside surface of said cannula housing, and further including an adhesive layer covering said underside surface.

* * * * *